(12) United States Patent
Lou

(10) Patent No.: US 10,782,277 B1
(45) Date of Patent: Sep. 22, 2020

(54) GAS DETECTION SYSTEM

(71) Applicant: Beijing Chengtian Advanced Technologies Ltd., Beijing (CN)

(72) Inventor: Jinghui Lou, Beijing (CN)

(73) Assignee: Beijing Chengtian Advanced Technologies Ltd., Beijing (CN)

( * ) Notice: Subject to any disclaimer, the term of this patent is extended or adjusted under 35 U.S.C. 154(b) by 0 days.

(21) Appl. No.: 16/586,717

(22) Filed: Sep. 27, 2019

(30) Foreign Application Priority Data

Sep. 24, 2019 (CN) .......................... 2019 1 0902886

(51) Int. Cl.
*G01N 33/00* (2006.01)
*H03M 1/12* (2006.01)

(52) U.S. Cl.
CPC ..... *G01N 33/0073* (2013.01); *G01N 33/0027* (2013.01); *H03M 1/12* (2013.01)

(58) Field of Classification Search
CPC ..................... G01N 33/0027; G01N 33/0073
USPC ............................................. 73/31.02, 31.03
See application file for complete search history.

(56) References Cited

U.S. PATENT DOCUMENTS

| 6,114,964 A * | 9/2000 | Fasano ............... G01N 33/0075 340/628 |
| 6,125,710 A * | 10/2000 | Sharp ....................... G01N 1/26 73/863.01 |
| 6,670,887 B2 * | 12/2003 | Dungan ............. G01N 33/0075 340/539.26 |
| 6,701,772 B2 * | 3/2004 | Kreichauf .............. G08B 21/12 73/23.2 |
| 2018/0041606 A1 * | 2/2018 | Luo ........................ G01D 21/00 |

\* cited by examiner

*Primary Examiner* — Daniel S Larkin
(74) *Attorney, Agent, or Firm* — Getech Law LLC; Jun Ye

(57) ABSTRACT

Aspects for a gas detection system are described herein. As an example, the aspects may include a master device and one or more slave sensor devices communicatively connected to the master controller device. The one or more slave sensor devices may be configured to respectively detect one or more types of gases to generate detection results, convert the detection results into detection signals, transmit the detection signals to the master controller device. The master controller device may be configured to receive the detection signals, generate a detection report based on the detection signals, and transmit the detection report to one or more external devices.

20 Claims, 5 Drawing Sheets

GAS DETECTION SYSTEM

BACKGROUND

Detecting hazardous gases conventionally may be implemented in a single standalone device that includes multiple gas sensors respectively configured to detect multiple types of gases. The multiple gas sensors are normally controlled by a main controller in the standalone device.

However, such standalone devices are not easily expandable when the user needs to detect a new type of gas since the gas sensors are pre-installed internally. In addition, gas detection systems are frequently brought to field work. It is preferable to limit the weight and size of the systems. Because of the limit on weight, the number of gas sensors is also limited.

Further, when the gas sensors are pre-installed, the gas detection system must include a controlling module, a data processor, a communication module, a power supply, etc. Cost-wise, it is undesirable to include all the components if the user only uses the gas detection system for one type of gas. The maintenance cost for the gas detection system is also relatively high since the entire system may need repair even if one of the gas sensors is malfunctioning.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

One example aspect of the present disclosure provides an example gas detection system. The example gas detection system may include a master controller device and one or more slave sensor devices communicatively connected to the master controller device. The one or more slave sensor devices respectively detect one or more types of gases to generate detection results, convert the detection results into detection signals, and transmit the detection signals to the master controller device. The master controller device, upon receiving the detection signals, may generate a detection report based on the detection signals, and transmit the detection report to one or more external devices.

Another example aspect of the present disclosure provides an example method for gas detection. The example method may include respectively detecting, by one or more slave sensor devices, one or more types of gases to generate detection results, wherein the one or more slave sensor devices are disseminated at one or more locations; converting, by the one or more slave sensor devices, the detection results into detection signals; transmitting, by the one or more slave sensor devices, the detection signals to a master controller device wirelessly connected to the one or more slave sensor devices; receiving, by the master controller device, the detection signals; generating, by the master controller device, a detection report based on the received detection signals; and transmitting, by the master controller device, the detection report to one or more external devices.

To the accomplishment of the foregoing and related ends, the one or more aspects comprise the features herein after fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which.

DETAILED DESCRIPTION

Figure 1:
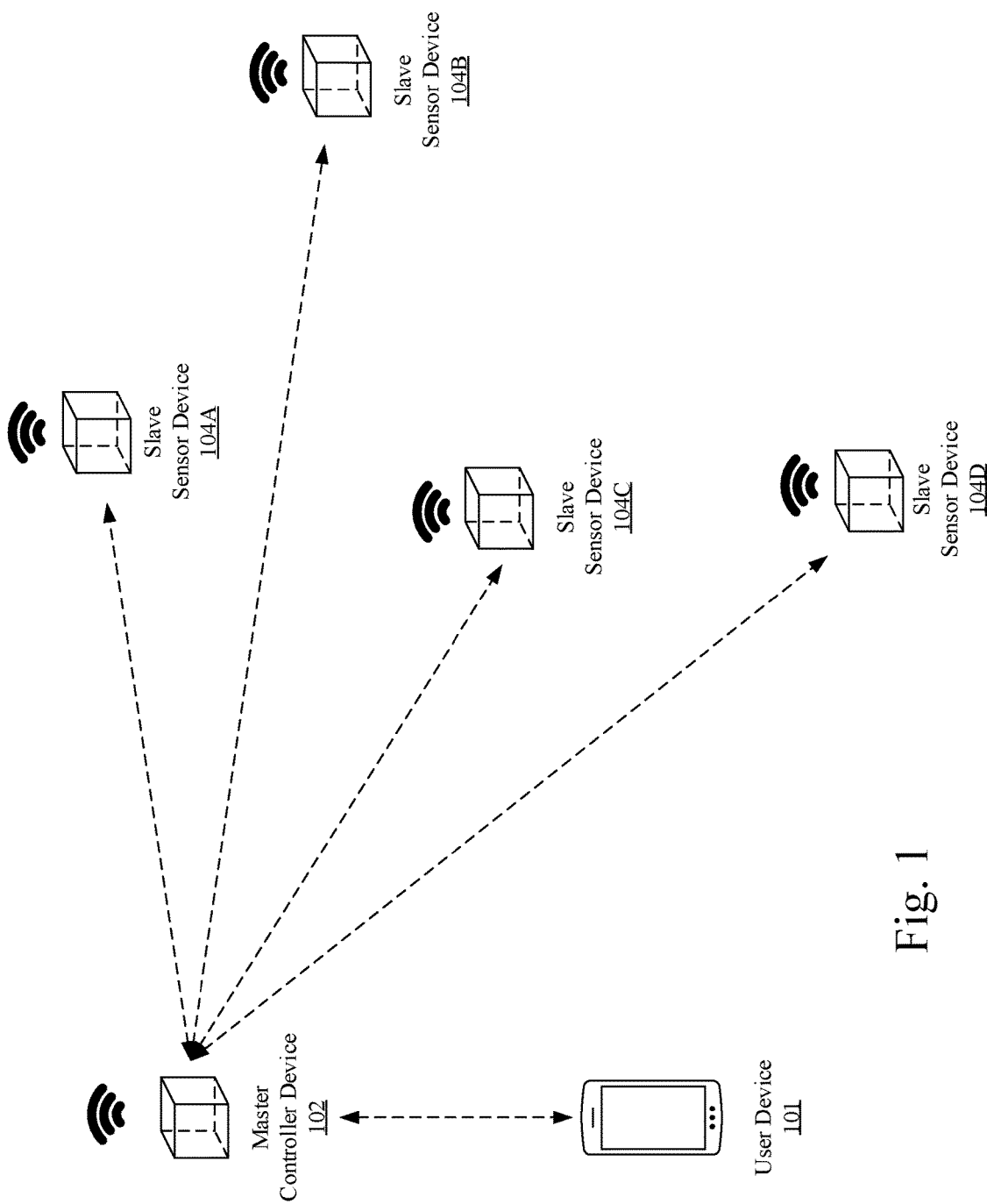
FIG. 1 illustrates an example gas detection system in accordance with the present disclosure.

Various aspects are now described with reference to the drawings. In the following description, for the purpose of explanation, numerous specific details are set forth in order to provide a thorough understanding of one or more aspects. It may be evident, however, that such aspect(s) may be practiced without these specific details.

In the present disclosure, the term "comprising" and "including" as well as their derivatives mean to contain rather than limit; the term "or", which is also inclusive, means and/or.

In this specification, the following various embodiments used to illustrate principles of the present disclosure are only for illustrative purpose, and thus should not be understood as limiting the scope of the present disclosure by any means. The following description taken in conjunction with the accompanying drawings is to facilitate a thorough understanding to the illustrative embodiments of the present disclosure defined by the claims and its equivalent. There are specific details in the following description to facilitate understanding. However, these details are only for illustrative purpose. Therefore, persons skilled in the art should understand that various alternation and modification may be made to the embodiments illustrated in this description without going beyond the scope and spirit of the present disclosure. In addition, for clear and concise purpose, some known functionality and structure are not described. Besides, identical reference numbers refer to identical function and operation throughout the accompanying drawings.

A gas detection system described hereinafter may include a master controller device and one or more slave sensor devices communicatively connected to the master controller device. The slave sensor devices may be respectively configured to detect one or more types of gases and to generate detection results. The detection results may be transmitted to the master controller device and the master controller device may generate a detection report based on the detection results.

In some examples, the slave sensor devices may be disseminated at different locations, e.g., by drones, and wirelessly communicated with the master controller device.

That is, the detection results may be transmitted to the master controller device wirelessly in accordance with wireless communication protocols, e.g., 3G, 4G, LTE, Bluetooth, Wi-Fi, etc.

In some other examples, the slave sensor devices may be physically connected to the master controller device. In these examples, the detection results may be transmitted to the master controller device via a communication interface.

Since each of the slave sensor devices is configured to detect one type of gas, a user may simply pick one or more of the slave sensor devices based on the type of gas that the user plans to detect. For example, in a home safety testing case, a user may select the slave sensor devices that are configured to detect carbon monoxide and natural gas respectively and ignore other slave sensor devices such that the weight and the power consumption of the entire system may be reduced. Similarly, the user may simply add another slave sensor device configured to detect a new type of gas if needed. When one of the slave sensor devices is malfunctioning, the user may simply replace the slave sensor device with a functioning slave sensor device. Thus, it becomes unnecessary to check and repair the entire system when one slave sensor device is malfunctioning.

Figure 4:
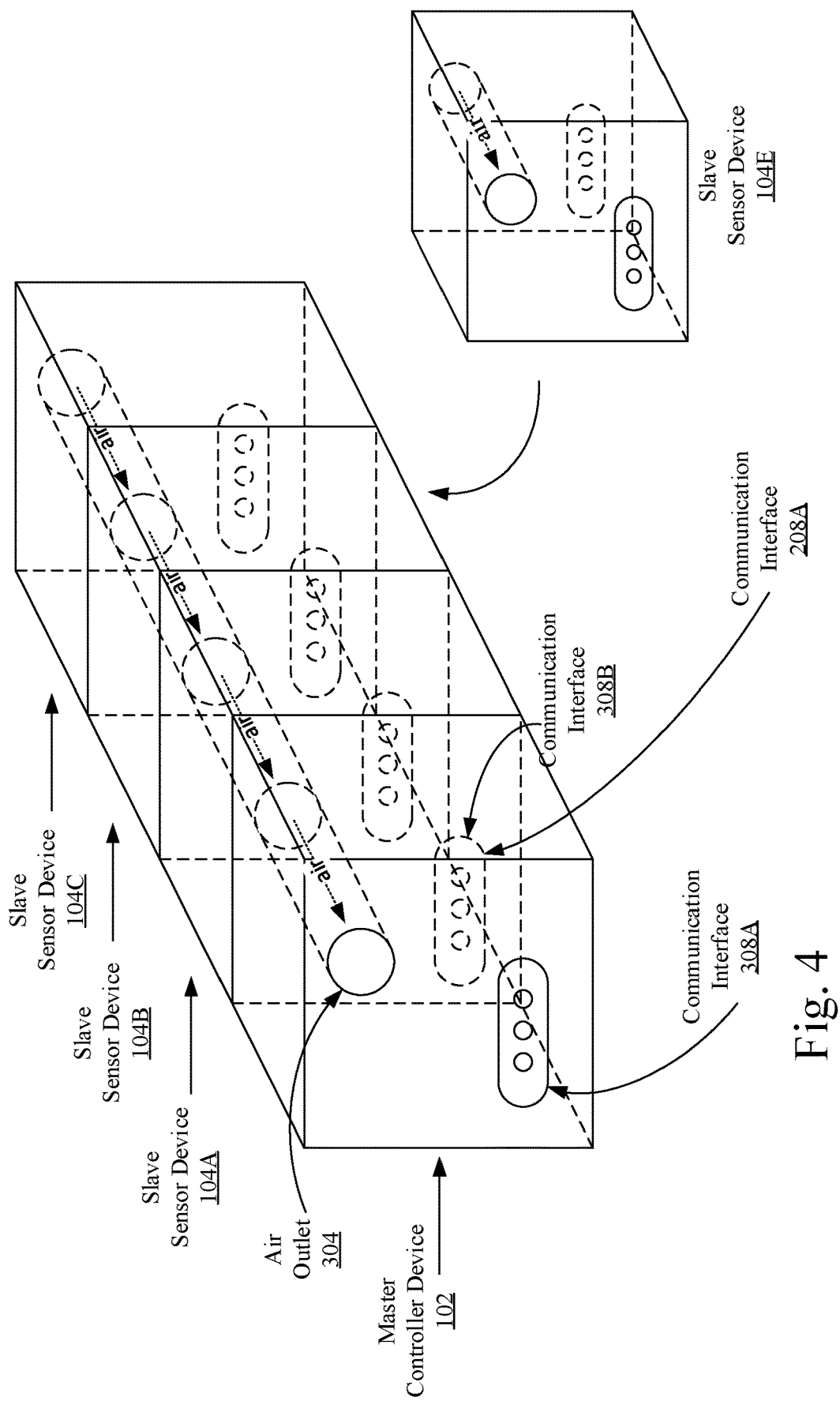
FIG. 4 illustrates the example gas detection system arranged in accordance with the present disclosure.

FIG. 1 illustrates an example gas detection system 100 in accordance with the present disclosure. As depicted, the example gas detection system 100 may include a master controller device 102 and one or more slave sensor devices, e.g., 104A, 104B, 104C, 104D, etc. (collectively "slave sensor devices 104"). The slave sensor devices 104 may be combinable with the master controller device 102 as illustrated in FIG. 4 and also detachable to be disseminated to one or more different locations.

As shown, the slave sensor devices 104 may be disseminated at different locations while being communicatively connected with the master controller device 102 such that the gas detection system 100 may detect one or more types of gases at the different locations. The master controller device 102 may be communicatively connected to a user device 101 in accordance with one or more wireless communication protocols, e.g., Bluetooth, WLAN, Zigbee, 3G, 4G, 5G, etc.

Upon receiving a detection instruction from the user device 101, the master controller device 102 may be configured to determine a sequence for the slave sensor devices 104 to initiate measurement of respective types of gases. For example, the master controller device 102 may determine that the slave sensor device 104A is the first to start the measurement and that the slave sensor devices 104B, 104C, and 104D start the measurement sequentially. Based on the sequence, the master controller device 102 may be configured to sequentially send initiation instructions to the respective slave sensor devices 104. That is, the master controller device 102 may send an initiation instruction to a slave sensor device when the master controller device 102 receives detection results from a previously sent initiation instruction. Alternatively, the master controller device 102 may be configured to transmit the initiation instructions including a preset initiation timepoint. For example, the initiation instructions may respectively include the time when each slave sensor device should start the measurement, e.g., the slave sensor device 104A starts measurement at 10:00 AM, the slave sensor device 104B starts measurement at 10:03 AM, the slave sensor device 104C starts measurement at 10:08 AM, and the slave sensor device 104D starts measurement at 10:11 AM.

When the slave sensor devices 104 receive the initiation instructions, the slave sensor devices 104 may be configured to respectively detect one or more types of gases. For example, the slave sensor device 104A may be configured to detect carbon monoxide; the slave sensor device 104B may be configured to detect benzene; the slave sensor device 104C may be configured to detect toluene; and the slave sensor device 104D may be configured to detect ozone. Further, the slave sensor devices 104 may be configured to convert the detection results into detection signals and transmit the detection signals back to the master controller device 102.

The master controller device 102 may be configured to integrate the detection results from the slave sensor devices 104 and generate a detection report including the detection results. An example detection report may include the detection results such as "carbon monoxide 1%; benzene 3.4%; toluene 4%; ozone 4.21%." The detection report may then be transmitted by the master controller device 102 to the user device 101 via the above mentioned the wireless communication protocols.

Figure 2:
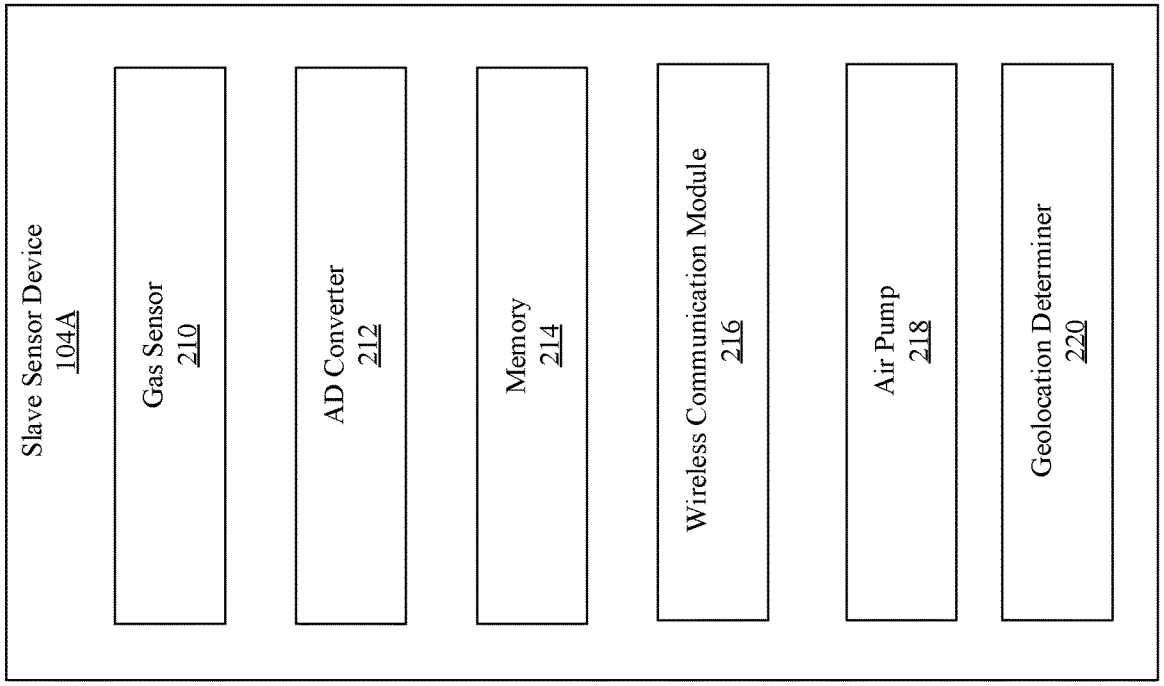
FIG. 2 illustrates an example slave sensor device in the example gas detection system in accordance with the present disclosure.
Figure 2:
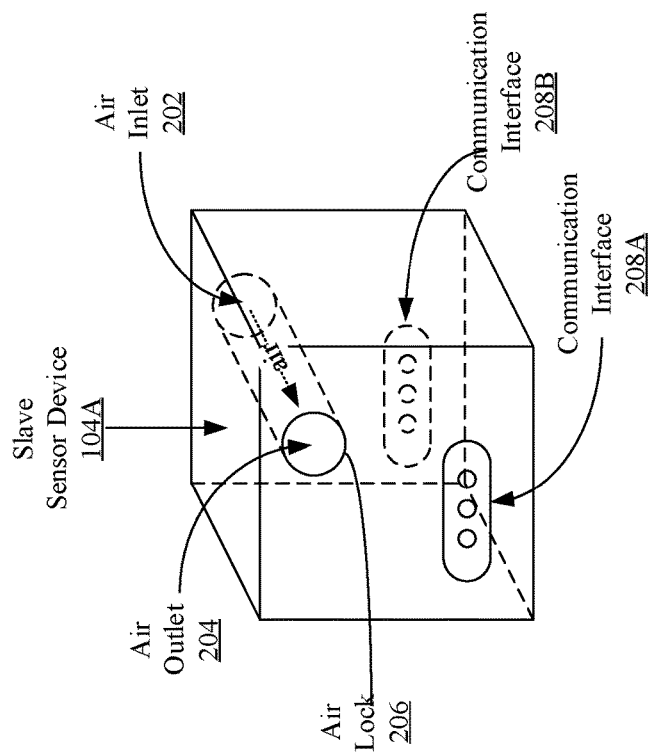

FIG. 2 illustrates an example slave sensor device 104A in the example gas detection system in accordance with the present disclosure. Other slave sensor devices 104 may include similar features to those of example slave sensor device 104A as described below. As depicted, the example slave sensor device 104A may include an air inlet 202 and an air outlet 204 that define an air path. When the slave sensor devices 104 are attached together, the air from the air outlet 204 may be drawn into an air inlet as illustrated in FIG. 4. The slave sensor device 104A may further include one or more air locks 206 attached to the air inlet 202 and the air outlet 204 to seal the air path when the slave sensor devices 104 are attached together. In some examples, the slave sensor device 104A may include an air pump 218 to circulate air in and out via the air inlet and the air outlet.

The slave sensor device 104A may further include a communication interface 208A and a communication interface 208B (collectively "communication interface 208") for directly wired communication with other slave sensor devices when the slave sensor devices 104 are attached together or with the master controller device 102. The communication interfaces 208 may be configured to transmit and receive data in accordance with one or more communication protocols, e.g., RS-485.

In some examples, the slave sensor device 104A may further include a gas sensor 210 configured to detect or measure one type of gas. For example, the gas sensor 210 may be configured to detect or measure one of carbon monoxide, benzene, toluene, and ozone. The gas sensor 210 may generate detection results in digital format or in analog format. The slave sensor device 104A may further include an analog-to-digital (AD) converter 212 configured to convert analog results generated by the gas sensors into digital format, e.g., detection signals. The detection results and the received initiation instructions may be stored in a memory 214. The memory 214 may be configured to further store a unique identification (ID) associated with the slave sensor device 104A. The unique ID may further include a type of the gas sensor (e.g., carbon monoxide sensor), a target of measurement (e.g., carbon monoxide), a starting timepoint (e.g., 10:00 AM), and a position in a predetermined measurement sequence (e.g., first to measure). The memory 214 may further store a current status of the gas sensor (e.g., properly working or malfunctioning), a timepoint of a most recent calibration, and one or more measurement results.

In addition, the slave sensor device 104A may further include a wireless communication module 216 configured to receive instructions from the master controller device 102 and transmit the detection signals to the master controller device 102 in accordance with the above-mentioned wireless communication protocols, e.g., Bluetooth, WLAN, Zigbee, 3G, 4G, 5G, etc.

In some examples, the slave sensor device 104A may further include a geolocation determiner 220, e.g., a Global Positioning System (GPS) module. The geolocation determiner 220 may be configured to receive information from satellites and to calculate a geolocation of the slave sensor device 104A. The geolocation may be transmitted to the master controller device 102 prior to receiving the initiation instruction. In other words, since the master controller device 102 may receive the geolocations of the respective slave sensor devices 104 prior to sending out initiation instructions, the master controller device 102 determine the sequence of sequence for the slave sensor devices 104 to initiate measurement based on the geolocations.

Figure 3:
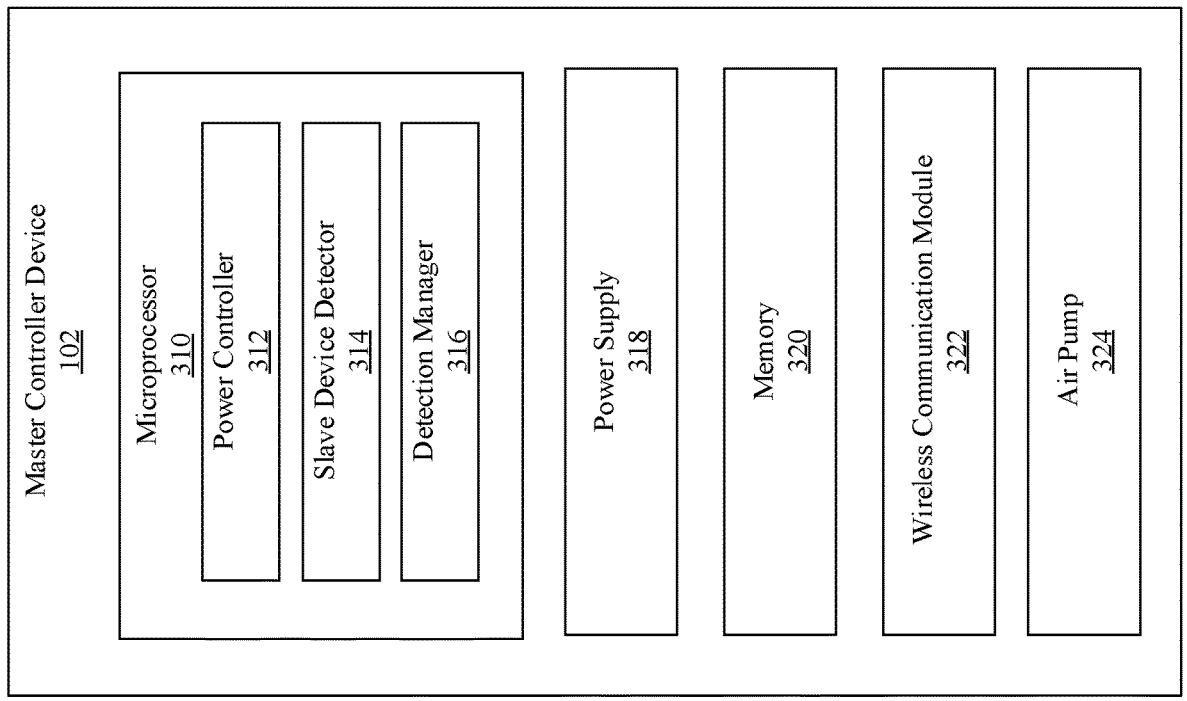
FIG. 3 illustrates an example master controller device in the example gas detection system in accordance with the present disclosure.
Figure 3:
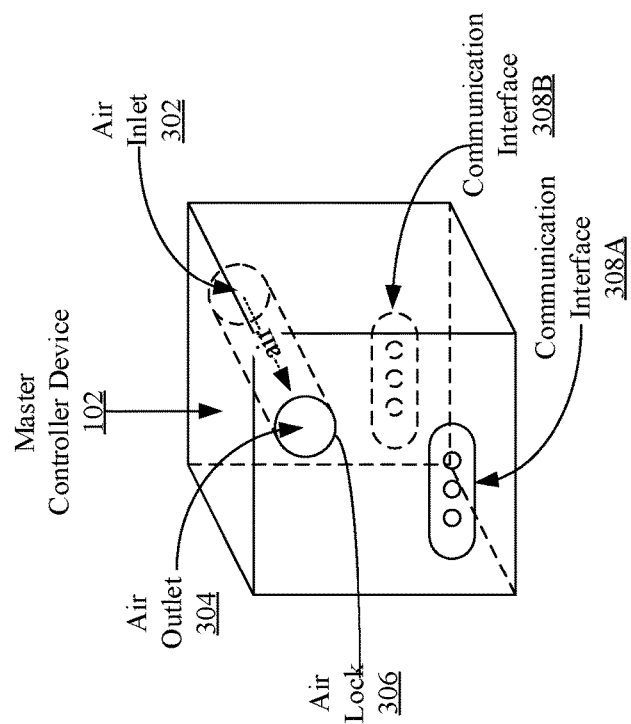

FIG. 3 illustrates an example master controller device 102 in the example gas detection system in accordance with the present disclosure. As depicted, the master controller device 102 may be implemented in a similar structure to the slave sensor devices 104 and may include similar features to those of the slave sensor devices 104 such that the master controller device 102 may be physically attached to the slave sensor devices 104 as shown in FIG. 4. For example, the master controller device 102 may similarly include an air inlet 302 and an air outlet 304 to form an air path such that air from an air outlet 204 of a slave sensor device may pass through the air path in the master controller device 102. An air lock 306 may also be included in the master controller device 102 to seal the air path between the master controller device 102 and one of the slave sensor devices 104. In addition, the master controller device 102 may include a communication interface 308A and a communication interface 308B (collectively "communication interfaces 308") for directly wired communication with the slave sensor devices 104. Similarly, the communication interfaces 308 may be configured to transmit and receive data in accordance with one or more communication protocols, e.g., RS-485.

Further, the master controller device 102 may include a microprocessor 310 configured to generate instructions and control data access. In more detail, the microprocessor 310 may include a power controller 312 configured to control the power of the master controller device 102 including turning on and off of the master controller device 102. The microprocessor 310 may further include a slave device detector 314 configured to detect and distinguish the slave sensor devices 104. For example, when the slave sensor devices 104 are communicatively connected to the master controller device 102, the master controller device 102 may receive the unique IDs from the slave sensor devices 104 and the corresponding geolocations. As such, the slave device detector 314 may recognize the slave sensor devices 104. The microprocessor 310 may further include a detection manager 316 configured to determine a sequence for the slave sensor devices 104 to initiate measurement of respective types of gases. Further, the detection manager 316 may be configured to calibrate the connected slave sensor devices 104 and store data related to the calibration such as an error history. The detection manager 316 may be further configured to combine the detection results received from slave sensor devices 104 and to generate a detection report based on the detection results.

The master controller device 102 may further include a power supply 318, e.g., a rechargeable or non-rechargeable battery.

Similar to the slave sensor devices 104, the master controller device 102 may include a memory 320, a wireless communication module 322, and an air pump 324. The memory 320 may be configured to store the detection results received from the slave sensor devices 104. The wireless communication module 322 may be configured to transmit the initiation instructions to the slave sensor devices 104, receive the detection results and the unique IDs of the slave sensor devices 104, and transmit the generated detection report to the user device 101. The air pump may be configured to circulate air from the air inlet 302 to the air outlet 304.

FIG. 4 illustrates the example gas detection system arranged in accordance with the present disclosure. As depicted, the master controller device 102 may be directly coupled with one or more slave sensor devices 104, e.g., the slave sensor devices 104A, 104B, and 104C as shown. In some examples, the air paths formed by the master controller device 102 and the slave sensor devices 104 may be aligned such that the air drawn into the air inlet of the slave sensor device 104C may be circulated out via the air outlet 304 of the master controller device 102. In at least some examples that the master controller device 102 does not include an air inlet and an air outlet, the master controller device 102 may be positioned such that the master controller device does not block the air path formed by the slave sensor devices 104.

In the example shown in FIG. 4, the communication interface 308B may be communicatively coupled to the communication interface 208A of the slave sensor device 104A. In this example, the detection results of the slave sensor devices 104 may be transmitted to the master controller device 102 via the respective communication interfaces 208 and communication interfaces 308. For example, the detection results generated by the slave sensor device 104C may be transmitted via the communication interfaces 208 to the master controller device 102, via the slave sensor devices 104B and 104A.

In the event that any of the slave sensor devices 104A, 104B, 104C is malfunctioning, the user may replace the malfunctioning slave sensor device with a working slave sensor device that is configured to detect the same type of gas, e.g., slave sensor device 104E, such that the maintenance of the entire system is simplified.

Figure 5:
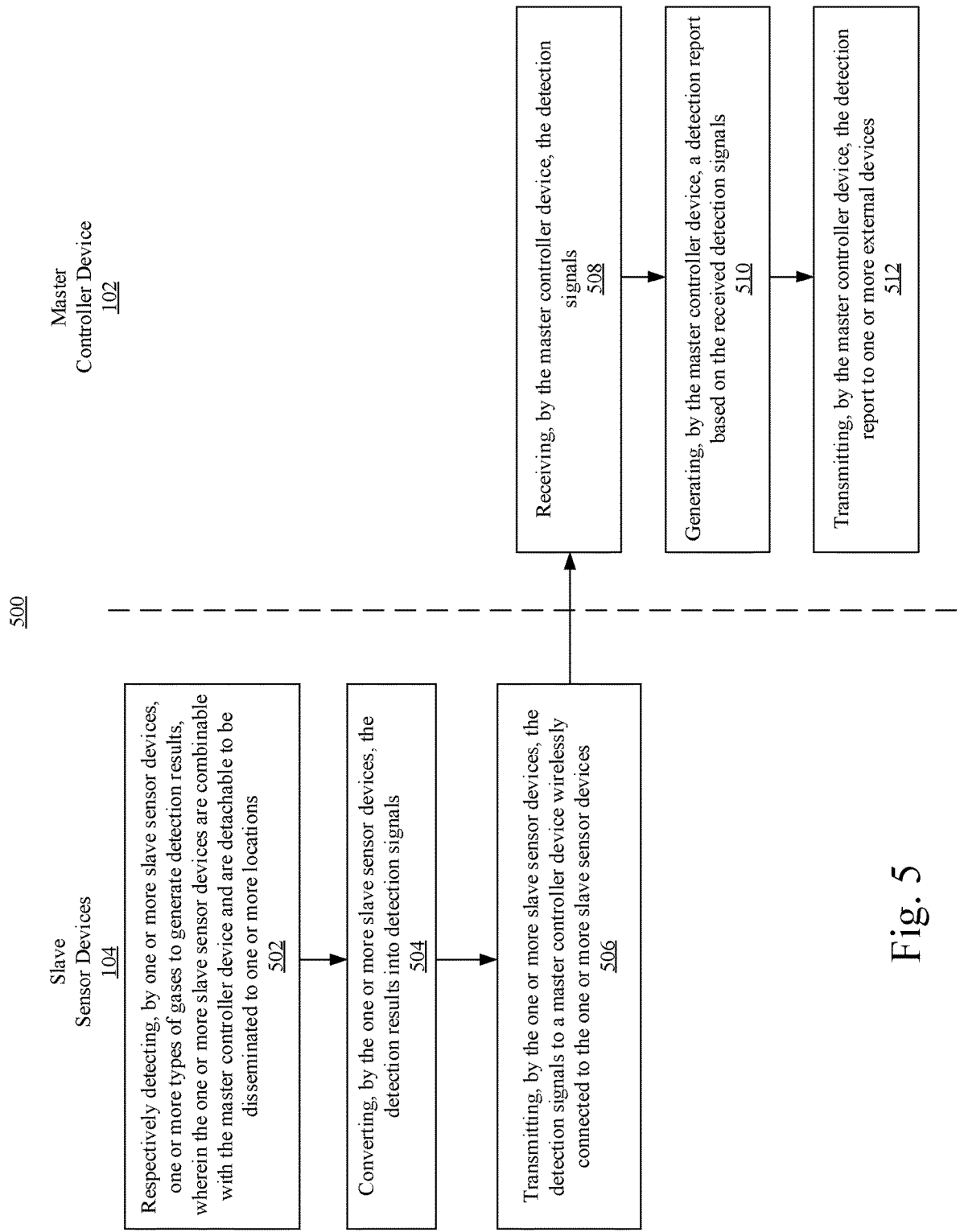
FIG. 5 illustrates is a flow chart of an example method for gas detection in accordance with the present disclosure.

FIG. 5 illustrates is a flow chart of an example method 500 for gas detection in accordance with the present disclosure. Operations included in the example method 500 may be performed by the components described in accordance with FIGS. 1-4.

At block 502, example method 500 may include respectively detecting, by one or more slave sensor devices, one or more types of gases to generate detection results. For example, the slave sensor devices 104 may be configured to respectively detect one or more types of gases. For example, the slave sensor device 104A may be configured to detect carbon monoxide; the slave sensor device 104B may be configured to detect benzene; the slave sensor device 104C may be configured to detect toluene; and the slave sensor device 104D may be configured to detect ozone. The one or more slave sensor devices 104 may be combinable with the master controller device and detachable to be disseminated to one or more locations.

At block 504, example method 500 may include converting, by the one or more slave sensor devices, the detection results into detection signals. For example, the AD converter 212 of the slave sensor device 104A may be configured to convert analog detection results generated by the gas sensors into digital format, e.g., detection signals.

At block 506, example method 500 may include transmitting, by the one or more slave sensor devices, the detection signals to a master controller device wirelessly connected to the one or more slave sensor devices. For example, the wireless communication module 216 of the slave sensor device 104A may be configured to transmit the detection signals to the master controller device 102 in accordance with the above-mentioned wireless communication protocols, e.g., Bluetooth, WLAN, Zigbee, 3G, 4G, 5G, etc.

At block 508, example method 500 may include receiving, by the master controller device, the detection signals. For example, the wireless communication module 322 of the master controller device 102 may be configured to transmit the initiation instructions to the slave sensor devices 104, receive the detection results and the unique IDs of the slave sensor devices 104.

At block 510, example method 500 may include generating, by the master controller device, a detection report based on the received detection signals. For example, the detection manager 316 may be configured to combine the detection results received from slave sensor devices 104 and to generate a detection report based on the detection results.

At block 512, example method 500 may include transmitting, by the master controller device, the detection report to one or more external devices. For example, the wireless communication module 322 of the master controller device 102 may be configured to transmit the generated detection report to the user device 101.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described herein that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

I claim:

1. A gas detection system, comprising:
a master controller device, and
one or more slave sensor devices communicatively connected to the master controller device,
   wherein the one or more slave sensor devices are combinable with the master controller device and are detachable to be disseminated;
   wherein the one or more slave sensor devices are configured to:
      respectively detect one or more types of gases to generate detection results,
      convert the detection results into detection signals, and
      transmit the detection signals to the master controller device;
   wherein the master controller device is configured to:
      receive the detection signals,
      generate a detection report based on the detection signals, and
      transmit the detection report to one or more external devices; and
   wherein each of the one or more slave sensor devices includes:
      an air inlet and an air outlet that define an air path, and
      one or more air locks configured to seal the air path when the one or more slave sensor devices are connected physically to each other.

2. The gas detection system of claim 1, wherein the one or more slave sensor devices are disseminated at one or more locations and wirelessly connected to the master controller device.

3. The gas detection system of claim 1, wherein the one or more slave sensor devices are located at a same location as the master controller device and physically combined with the master controller device via a hardware interface.

4. The gas detection system of claim 1, wherein each of the one or more slave sensor devices includes a gas sensor configured to measure one of the one or more types of gases.

5. The gas detection system of claim 4, wherein each of the one or more slave sensor devices include a memory configured to store a unique identification (ID) associated with the slave sensor device.

6. The gas detection system of claim 5, wherein the unique ID includes a type of the gas sensor, a target of measurement, a starting timepoint, and a position in a predetermined measurement sequence.

7. The gas detection system of claim 5, wherein the memory is further configured to store a current status of the gas sensor, a timepoint of a most recent calibration, and one or more measurement results.

8. The gas detection system of claim 1, wherein each of the one or more slave sensor devices includes an analog-to-digital (AD) converter configured to convert the detection results into the detection signals.

9. The gas detection system of claim 1, wherein each of the one or more slave sensor devices includes a communication interface in accordance with one or more communication protocols.

10. The gas detection system of claim 1, wherein each of the one or more slave sensor devices includes an air pump to circulate air in and out via the air inlet and the air outlet.

11. The gas detection system of claim 1, wherein each of the one or more slave sensor devices includes a geolocation determiner configured to determine a geolocation of the slave sensor device.

12. The gas detection system of claim 1, wherein the master controller device is configured to determine a sequence of the one or more slave sensor devices to initiate measurement.

13. The gas detection system of claim 1, wherein the master controller device includes:
an air inlet and an air outlet,
one or more air locks to seal an air path defined by the air inlet and the air outlet when the master controller device is physically connected to one of the one or more slave sensor device, and
an air pump to receive air from the connected slave sensor device.

14. The gas detection system of claim 1, wherein the master controller device is configured to transmit the detection report to the one or more external devices wirelessly in accordance with one or more communication protocols.

15. The gas detection system of claim 1, wherein each of the one or more slave sensor devices includes an air processing device configured to dry and dedust air drawn via the air inlet.

16. A method for gas detection, comprising:
respectively detecting, by one or more slave sensor devices, one or more types of gases to generate detection results, wherein the one or more slave sensor devices are combinable with the master controller device and are detachable to be disseminated to one or more locations;
converting, by the one or more slave sensor devices, the detection results into detection signals;
transmitting, by the one or more slave sensor devices, the detection signals to a master controller device wirelessly connected to the one or more slave sensor devices;
receiving, by the master controller device, the detection signals;
generating, by the master controller device, a detection report based on the received detection signals; and
transmitting, by the master controller device, the detection report to one or more external devices,
wherein each of the one or more slave sensor devices includes:
an air inlet and an air outlet that define an air path, and
one or more air locks configured to seal the air path when the one or more slave sensor devices are connected physically to each other.

17. The method of claim 16, further comprising measuring, by a gas sensor of each of the one or more slave sensor devices one of the one or more types of gases.

18. The method of claim 16, further comprising converting, by an analog-to-digital (AD) converter, the detection results into the detection signals.

19. The method of claim 16, further comprising determining, by the master controller device, a sequence of the one or more slave sensor devices to initiate measurement.

20. A gas detection system, comprising:
a master controller device, and
one or more slave sensor devices communicatively connected to the master controller device,
wherein the one or more slave sensor devices are combinable with the master controller device and are detachable to be disseminated;
wherein the one or more slave sensor devices are configured to:
respectively detect one or more types of gases to generate detection results,
convert the detection results into detection signals,
transmit the detection signals to the master controller device;
wherein the master controller device is configured to:
receive the detection signals,
generate a detection report based on the detection signals, and
transmit the detection report to one or more external devices; and
wherein the master controller device includes:
an air inlet and an air outlet,
one or more air locks to seal an air path defined by the air inlet and the air outlet when the master controller device is physically connected to one of the one or more slave sensor device, and
an air pump to receive air from the connected slave sensor device.

\* \* \* \* \*